United States Patent [19]
Vogl

[11] Patent Number: 5,155,758
[45] Date of Patent: Oct. 13, 1992

[54] PORTABLE DEVICE FOR FACILITATING THE PERFORMANCE OF RADIOGRAPHIC PROCEDURES

[76] Inventor: Thomas Vogl, 33265 N. Sears Blvd., Wildwood, Ill. 60030

[21] Appl. No.: 511,389

[22] Filed: Apr. 19, 1990

[51] Int. Cl.⁵ .............................................. H05G 1/00
[52] U.S. Cl. ........................................ 378/209; 5/614; 5/611; 378/208
[58] Field of Search ............... 378/209, 208, 177, 179; 5/62

[56] References Cited

U.S. PATENT DOCUMENTS

| | | | |
|---|---|---|---|
| 1,252,276 | 1/1918 | McClain | 5/62 |
| 2,828,172 | 3/1958 | McDonald | 378/209 |
| 2,989,634 | 6/1961 | Ould | 378/177 |
| 3,818,516 | 6/1974 | Hopper et al. | 378/209 |
| 4,193,148 | 3/1980 | Rush | 378/177 |

Primary Examiner—Craig E. Church
Attorney, Agent, or Firm—Wood, Phillips, Van Santen, Hoffman & Ertel

[57] ABSTRACT

A portable device for facilitating the performance of radiographic procedures. The device has a free-standing base; a patient support table with a substantially flat torso support surface; structure mounting the table to the base for selective movement relative to the base between (a) a first operating position wherein the torso support surface is in a substantially horizontal orientation to support a patient in a prone position and (b) a set-up/second operating position in which the torso support surface is substantially vertically oriented so that a patient in an upright position can lean against the torso support surface; and structure for fixing the position of the table relative to the base.

16 Claims, 2 Drawing Sheets

PORTABLE DEVICE FOR FACILITATING THE PERFORMANCE OF RADIOGRAPHIC PROCEDURES

BACKGROUND OF THE INVENTION

1. Field of the Invention

This invention relates to support devices for patients to facilitate the performance of radiographic procedures and, more particularly, to a portable, collapsible device with a pivotable table that can be used to (a) perform radiographic procedures with a patient supported selectively in upright and recumbent positions and (b) facilitate situation of a patient in the prone position.

2. Background Art

Designers of radiographic patient support devices contend with the competing objectives of affording a very versatile structure, yet one which is not unduly burdensome and, ideally, portable. Heretofore, these devices have been made either versatile or portable, but not both.

One desirable feature of radiographic patient support devices is a pivotable table upon which the patient is supported. This feature is desirable because it allows radiographic procedures to be performed on a patient either in a vertical position, as with chest and abdominal radiography, or a horizontal position, for various other radiographic procedures. These structures are generally expensive, very cumbersome, and practical only as permanently installed structures in hospitals, clinics and physicians' offices.

Truly portable devices are generally one-dimensional. That is, they have a fixed, horizontal table orientation. The performance of certain radiographic procedures on such tables is thus impossible.

A further drawback with the prior art "portable" tables is that, while they are technically portable, they require significant on-site assembly/disassembly. The inconvenience of this is apparent and makes such structures undesirable.

A further drawback with fixed table structures is that it is very difficult for the patient to become situated on the elevated, horizontal support surface. Patients that are short or disabled will generally find it inconvenient to climb onto the table and will frequently require assistance to do this. One solution to this problem is to fix the table at a lower height which, while convenient for the patient, is inconvenient for the physician. Another solution to this problem is to incorporate structure to raise and lower the table. However, heretofore, the structures to accomplish this have been sufficiently cumbersome and expensive that it has been impractical to incorporate into a portable table.

In spite of the deficiencies of the prior art portable tables, they remain in great demand. There is a significant market for portable tables which may be taken into the field and used on site in conjunction with portable X-ray machines to perform routine radiographic procedures.

SUMMARY OF THE INVENTION

The present invention is specifically directed to overcoming the above enumerated problems in a novel and simple manner.

According to the invention, a portable device is provided for facilitating the performance of radiographic procedures. The device has a free-standing base; a patient support table with a substantially flat torso support surface; structure mounting the table to the base for selective movement relative to the base between (a) a first operating position wherein the torso support surface is in a substantially horizontal orientation to support a patient in a prone position and (b) a set-up/second operating position in which the torso support surface is substantially vertically oriented so that a patient in an upright position can lean against the torso support surface; and structure for fixing the position of the table relative to the base.

With the inventive structure, the patient can lean against the torso support surface, whereupon the table with the patient thereagainst can be pivoted relative to the base to position the table in the first operating position therefor and the patient in a prone position for performing a radiographic procedure.

The invention also contemplates the provision of a foot support surface extending transversely to the plane of the torso support surface. The foot support surface positively maintains the patient in a desired vertical position, wherein certain radiographic procedures can be conveniently performed, and facilitates pivoting of the patient from the vertical to the prone position. The inventive structure affords a range of different positions for the torso support surface between substantially horizontal and vertical and at the same time affords a convenient way for disabled, short patients to get into a prone position on the table.

Rollers are preferably provided on the bottom of the base to facilitate movement thereof across a support surface for the device. The device can thus be readily moved. Preferably at least one of the wheels can be locked, when desired, to prevent movement of the base on the support surface therefor. Another aspect of the invention is the provision of a transparent material to define at least part of the torso support surface. In a typical procedure, an image receptor is located beneath the patient. The transparent surface allows the operator to see the exact location of the image receptor with respect to the patient on the torso support surface.

In a preferred form, a carriage is provided on a frame for the table to carry the image receptor and is mounted for sliding movement between the ends of the table. The physician can readily select the desired position for the carriage to appropriately position the image receptor.

In a preferred form of the invention, the entire torso support surface on the table is radio-translucent and at least partially transparent.

Another aspect of the invention is the incorporation of a collapsible feature into the base. A plurality of links are interconnected to define the base. In one form of the invention, the base has a bottom section and a first link with opposite ends connected pivotably to the bottom section and table and a second link with opposite ends pivotably connected to the first link and bottom section. One of the opposite ends of the second link is removably connected so that upon disengagement thereof, the table can be pivoted on the other link to a compact, collapsed position adjacent to the bottom section of the base.

The invention contemplates fixing the position of the table anywhere through the range of pivoting of the table. Preferably, the table is pivotable from a vertical position to an over-horizontal position, i.e. through greater than 270°. To fix the table position, an elongate link is provided connecting between the table and the base. The link is made up of first and second parts engageable with each other so as to be movable lengthwise relative to each other. Structure is provided to fix the relative lengthwise positions of the first and second link parts. Each of the first and second link parts is elongate. The fixing structure consists of a locking plate having a through bore with an axis with one of the first and second link parts extending through the locking plate bore, structure for limiting lengthwise movement of the locking plate relative to the other of the first and second link parts, and structure for canting the plate relative to the one link part so that the length of the one link part and plate bore axis can be misaligned and resultingly the one link part binds within the locking plate bore to thereby fix the relative positions of the first and second link parts. In a preferred form, there are two similarly acting locking plates, which are normally biased away from each other to a locked position for the link parts. The mechanism is thus failsafe. Through a remote actuator, the bias force holding the plates apart is overcome so that the one link part can slide through the plate bores.

Another aspect of the invention is the provision of a trough on at least one side of the table to collect fluids and contaminants on the table surface. Accumulated fluids, and the like, can be directed to an appropriate point of disposal.

DETAILED DESCRIPTION OF THE DRAWINGS

Figure 1:
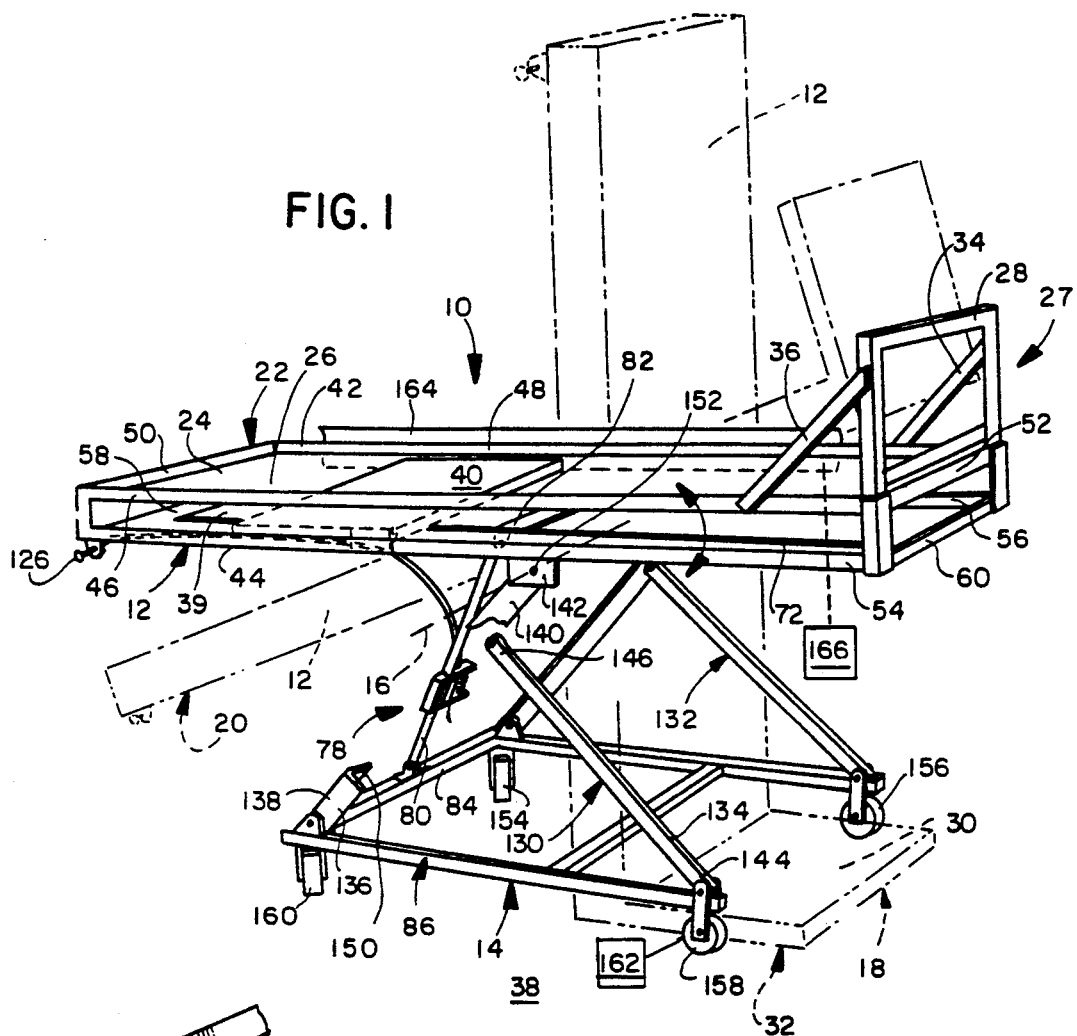
FIG. 1 is a perspective view of a portable device for facilitating the performance of radiographic procedures according to the present invention and showing a patient support table in three different positions relative to a support base therefor.
Figure 4:
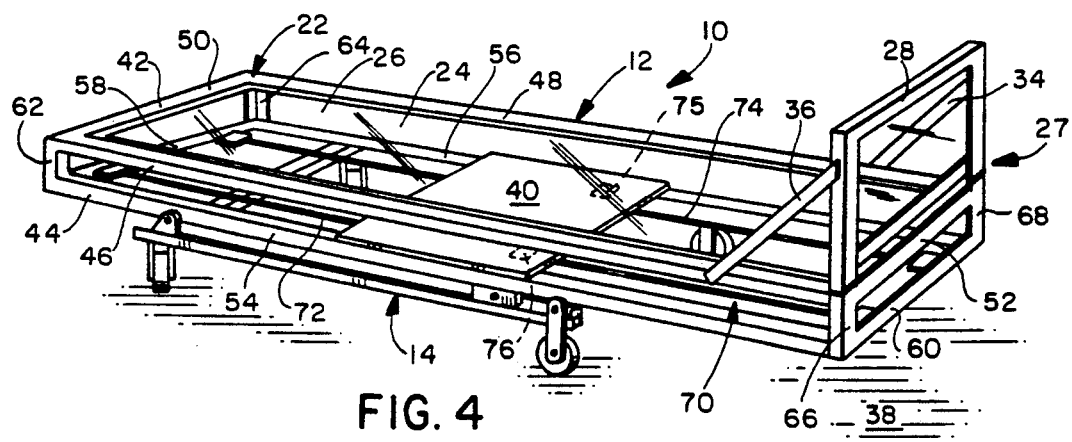
FIG. 4 is a perspective view of the device in a collapsed state.

A preferred form of portable device for facilitating the performance of radiographic procedures, according to the present invention, is shown at 10 in FIGS. 1 and 4. The device 10 consists of a patient support table 12 and a base therefor at 14. The table 12 is pivotable relative to the base 14 about a horizontal, laterally extending axis 16 between a vertical position, shown in phantom at 18 in FIG. 1, and an over-horizontal position, shown in phantom at 20 in FIG. 1. The entire range of pivoting for the table 12 is thus in excess of 270°.

The table 12 has a metal frame 22 which supports a rectangular sheet of transparent, radio-translucent polycarbonate material 24. The sheet 24 defines a torso support surface 26 which is substantially flat and horizontal with the table in the solid line position of FIG. 1. In the solid line position of FIG. 1, the table 12 supports a patient on the surface 26 in a prone and elevated position.

The table 12 has a foot support assembly at 27 with a rectangular frame portion 28 generally at right angles to the plane of the support surface 26. The frame portion 28 has a flat foot support surface 30 thereon. The foot support assembly 27 is rigidly attached to the metal frame 22 and reinforced by angled braces 34, 36. The purpose of the foot support assembly 32 is two-fold. With the table 12 in the vertical position at 18 in FIG. 1, the foot support surface 30 is adjacent to the surface 38 supporting the device 10. The patient can conveniently step up onto the surface 30. In this position, it is possible to perform radiographic procedures, as described more fully below.

The foot support assembly 32 also safely supports the patient as the table 12 is pivoted from the vertical position at 18, in a counterclockwise position in FIG. 1, to the solid line position for the table 12 in FIG. 1, wherein the patient resides in an elevated, prone position. This obviates having the user climb up onto the table 12 in the solid line position of FIG. 1 and the need for steps, or the like, to enable the patient to move onto the elevated table 12. Once the radiographic procedure is completed, the table 12 can be pivoted in a clockwise direction about the axis 16 to let the patient simply walk off the foot support assembly 27 on the vertically positioned table 12.

The frame 22 also provides a space 40 for a translatable carriage 40 beneath the torso support surface 26. The carriage 40 supports an image receptor which cooperates with a portable X-ray machine during a radiographic procedure. The frame 22 is made up of two separate, rectangular frame assemblies 42, 44 in vertically spaced relationship. The upper frame assembly 42 has spaced side rails 46, 48 and end rails 50, 52, each preferably made from metal angle iron material. The bottom frame assembly 44 has similar side rails 54, 56 and end rails 58, 60. The frame assemblies 42, 44 are rigidly interconnected at the corners thereof by uprights 62, 64, 66, 68 to define a space 70 between the assemblies 42, 44, within which the carriage 40 can move. Laterally spaced tie/guide rods 72, 74 run parallel to each other and connect to the end rails 58, 60 on the lower frame assembly 44. Cooperating guide elements 74, 76, shown schematically in FIG. 4, are provided on the underside of the carriage 40 and guide translatory movement of the carriage 40 between the ends of the table 12. The carriage 40 is of conventional construction, and thus detailed description of the same is omitted herefrom.

Figure 2:
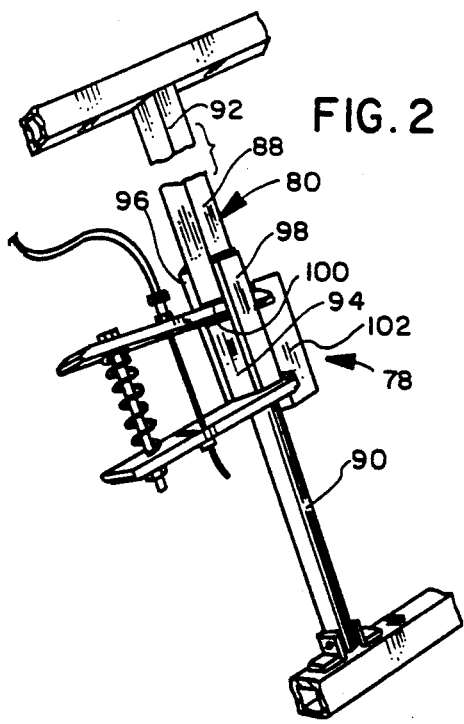
FIG. 2 is an enlarged perspective view of a locking structure for fixing the position of the table relative to the base.
Figure 3:
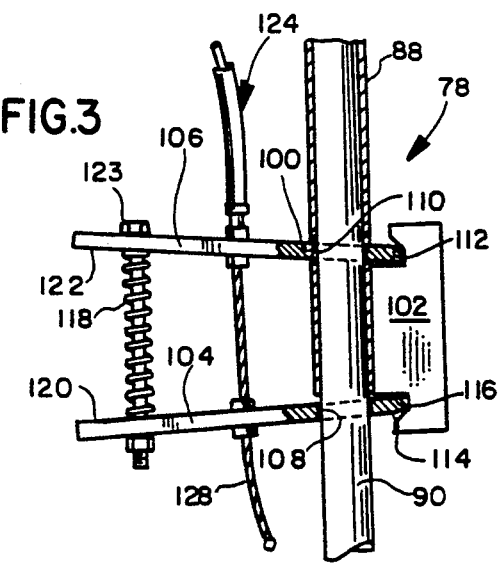
FIG. 3 is an end elevation view of the locking mechanism of FIG. 2.

To fix a desired position of the table 12 relative to the base 14, a locking mechanism is provided at 78 and is clearly shown in FIGS. 1-3. The locking mechanism 78 consists of an elongate link 80 connecting pivotably to a cross bar 82 on the underside of the table frame 22 and pivotably to a cross bar 84 on a bottom section 86 of the base 14. The link 80 consists of cooperating upper and lower link parts 88, 90, respectively, which are telescopingly engaged with each other and movable lengthwise relative to each other to select the effective length of the link 80 to thereby fix the table 12 in a desired position.

In the illustrated lock mechanism 78, the lower link part 90 fits within the upper link part 88. The upper link part 88 has a first part 92 and a second part 94 joined by two plates 96, 98 welded to opposite surfaces of the upper link part 88 so as to define a unitary structure with a through opening 100 between the first and second parts 92, 94. The link part 94 carries a T-shaped plate anchor 102 fixedly thereon.

First and second metal locking plates 104, 106, each generally rectangular in shape, cooperate with the link parts 88, 90 to fix the relative position therebetween. The locking plate 104 has a through bore 108 and the locking plate 106 a through bore 110 matched closely to the cross section of the lower link part 90, which cross section is generally circular.

To effect assembly of the locking mechanism 78, the locking plate 106 is directed through the opening 100 in the upper link part 88 and into a U-shaped seat 112 in the plate anchor 102 so that the bore 100 is centered on the longitudinal axis of the link part 88. The end 114 on the other plate 104 is directed into a U-shaped seat 116 in the plate anchor 102 so that the bore 108 in the plate 104 also aligns with the central axis of the link part 88. The lower link part 90 is then directed consecutively through the bore 108 in the looking plate 104, into the upper link part 88 and through the bore 110 in the locking plate 106. The seats 112, 116 are configured to allow the plates 104, 106 to be pivoted slightly between an assembly position, wherein the axes of the bores 108, 110 in the plates 104, 106 are aligned with the central axis/length of the link 80, and a canted position, as shown in FIG. 3, wherein the axes are misaligned so that the lower link part 90 binds within the plate bores 108, 110. The plates 104, 106 are normally biased away from each other by a coil spring 118 interposed between facing surfaces 120, 122 on the plates 104, 106, respectively. The spring 118 is held in its operative position by a bolt 122 extending through the spring 118 and both plates 104, 106.

FIG. 3 depicts the normal, locked position for the locking mechanism 78. To unlock the mechanism 78, the plates 104, 106 are urged towards each other against the bias of coil spring 118 to align the axes of the bores 108, 110 with the length of the link 80. This is accomplished preferably through a conventional coaxial cable arrangement 124 with the remote actuator 126 that is movable back and forth to extend and retract an inner core cable 128.

Figure 5:
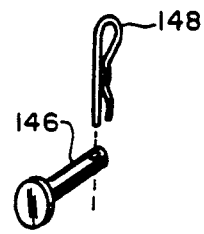
FIG. 5 is a perspective view of a removable pin structure for releasably connecting links on the base and table.

Another feature of the present invention is the provision of structure to collapse the base 14 to the FIG. 4 configuration. The base 14 has laterally spaced triangular shaped supports 130, 132 acting between the table 12 and the base bottom section 86. These two supports 130, 132 are substantially the same and description herein will be limited to exemplary support 132. The support 130 consists of a first link 134 having a square cross section and an angle iron link 136. The angle iron link 136 is pivotably connected at one end 138 to the bottom section 86 and at its other end 140 to a depending flange 142 on the table 12. The lower end 144 of link 134 is pivotably connected to the base bottom section 86 and the upper end 146 thereof is pivotably connected to the link 136 below its upper end 140. A removable pin, such as that 146 in FIG. 5, is preferably employed at each pivotable connection for the links 134, 136. A press fit formed wire retainer 148 (FIG. 5) prevents inadvertent removal of the pins 146.

The device 10 can be readily collapsed by removing three pins—those at the connection between the link 134 and link 136, and the counterpart therefor on the other support 132, and the pin 146 at either the top or bottom of the link 80. Once this occurs, the link 134 and its counterpart on support section 132 can be pivoted downwardly against the bottom section 86 after which the table 12 can be pivoted about link 136 and its counterpart on the support section 132 so that the rearwardly facing surface 150 on the link 136 facially abuts the link 134. The size of the angle iron for the link 136 is chosen so that it will flushly bear on the link 134 in a collapsed position for the device 10. The support section 132 collapses in similar fashion on the other side of the device 10.

To assure smooth pivoting of the table 12 on the base 14, sealed bearings 152 are preferably employed at the juncture of the link 136 and flange 142 and the counterpart structure on the other side of the table 12.

To facilitate movement of the device 10, rollers 154, 156, 158, 160 are provided on the bottom of the base 14. A conventional-type locking mechanism, shown schematically at 162 in FIG. 1, is employed to fix the position of at least one of the rollers 154, 156, 158, and 160, to hold the device 10 in a stationary position.

Another aspect of the invention is the provision of a trough 164 on at least one side of the table 12. The trough 164 is designed to collect any fluid and/or contaminant that has accumulated on the support surface 26 on the table 12. The fluid/contaminant can be accumulated in the trough 164 and delivered to an appropriate discharge location, shown schematically at 166 in FIG. 1.

It can be seen that the invention affords a structure that is truly portable, one that can be simply collapsed for transportation and/or storage and reassembled, and one that is very versatile in its function as a support for a patient in both vertical and horizontal orientations.

The foregoing disclosure of specific embodiments is intended to be illustrative of the broad concepts comprehended by the invention.

I claim:

1. A portable device for positioning a radiographic subject selectively in any one of a number of angular positions from the vertical to the horizontal, said device comprising:

a free standing base;

a patient support table including a substantially flat torso support surface with spaced ends and a foot support surface extending transversely to the plane of the torso support surface;

means mounting the table to the base for selective movement relative to the base between (a) a first operating position wherein the torso support surface is in a substantially horizontal orientation to support a patient in a prone position and (b) and setup/second operating position in which the torso support surface is substantially vertically oriented so that a patient may be conveniently loaded on the portable device by standing on the foot support surface in an upright position, whereupon the table with the patient thereon can be pivoted relative to the base to orient the table in the first operating position and the patient in a desired prone position for performing a radiographic procedure, there being a single, laterally extending pivot axis about which the table is movable relative to the base between its first and second positions with the pivot axis located at a midportion between the ends of the torso support surface, said table mounting means comprising first and second laterally spaced supports, with each said first and second support having first and second links extending upwardly from the base and defining a triangular shape; and means for fixing the table relative to the base with the table, said table fixing means comprising extensible means extending between the patient support table and one of the base and table mounting means for fixing the patient support table selectively in a plurality of different positions relative to the base.

2. The portable device according to claim 1 including roller means on the base for facilitating movement of the base relative to a support surface therefor.

3. The portable device according to claim 1 wherein the torso support surface is at least partially transparent to permit an operator of radiographic equipment used in conjunction with the portable device to view the radiographic equipment beneath a patient supported on the table to facilitate proper positioning of the radiographic equipment relative to the patient.

4. The portable device according to claim 1 wherein the patient support table comprises a frame and a radiotranslucent material supported on said frame and defining at least a part of said torso support surface.

5. The portable device according to claim 1 wherein said support table has a frame with vertically spaced rails defining therebetween a space for radiographic equipment such as an X-ray cassette.

6. The portable device according to claim 1 wherein means are provided for connecting the links so that the links can be folded relative to each other to collapse the table downwardly and compact the overall structure as for transportation and/or storage.

7. The portable device according to claim 1 wherein the table is pivotable relative to the base through in excess of 270°.

8. The portable device according to claim 1 wherein the base includes a bottom section, said first links each have opposite ends connected pivotably to the bottom section and table and said second links each have opposite ends pivotably connected to a first link and the bottom section, one said opposite end of the second links being removably connected so that upon disengagement thereof the table can be pivoted to a collapsed position adjacent to the bottom section of the base.

9. The portable device according to claim 1 wherein the means for fixing the table comprises an elongate link connecting between the table and the base and made up of first and second engaging parts movable lengthwise relative to each other and means are provided for fixing the relative lengthwise positions of the first and second link parts.

10. The portable device according to claim 1 including a trough on said table for accumulating fluids and contaminants from on the table.

11. The portable device according to claim 2 wherein the roller means comprises a plurality of rollers with means for locking at least one of the rollers to prevent rolling of the base on a support surface therefor.

12. The portable device according to claim 9 including means remote from said fixing means for the first and second link parts for actuating the table fixing means.

13. A portable device for positioning a radiographic subject in a plurality of angular positions from the vertical to the horizontal, said device comprising:
a free standing base;
a patient support table including a substantially flat torso support surface and a foot support surface extending transversely to the plane of the torso support surface;
means mounting the table to the base for selective movement relative to the base between (a) a first operating position wherein the torso support surface is in a substantially horizontal orientation to support a patient in a prone position and (b) a setup/second operating position in which the torso support surface is substantially vertically oriented so that a patient may stand on the foot support surface in an upright position, whereupon the table with the patient thereon can be pivoted relative to the base to orient the table in the first operating position and the patient in a desired prone position for performing a radiographic procedure; and
means for fixing the table relative to the base with the table in a desired position,
wherein the means for fixing the table comprises an elongate link connecting between the table and the base and made up of first and second engaging parts movable lengthwise relative to each other and means are provided for fixing the relative lengthwise positions of the first and second link parts,
wherein the first and second links are elongate, the table fixing means includes a locking plate having a through bore with an axis with one of the first and second link parts extending through the locking plate bore, means for limiting lengthwise movement of the locking plate relative to the other of the first and second link parts and means for canting the plate relative to the one link part so that the length of the one link part and plate bore axis misalign and resultingly the one link part binds within the locking plate bore to thereby fix the relative positions of the first and second link parts.

14. A portable device according to for positioning a radiographic subject in a plurality of angular positions from the vertical to the horizontal, said device comprising:
a free standing base;
a patient support table including a substantially flat torso support surface and a foot support surface extending transversely to the plane of the torso support surface;
means mounting the table to the base for selective movement relative to the base between (a) a first operating position wherein the torso support surface is in a substantially horizontal orientation to support a patient in a prone position and (b) a setup/second operating position in which the torso support surface is substantially vertically oriented so that a patient may stand on the foot support surface in an upright position, whereupon the table with the patient thereon can be pivoted relative to the base to orient the table in the first operating position and the patient in a desired prone position for performing a radiographic procedure; and
means for fixing the table relative to the base with the table in a desired position,
wherein the means for fixing the table comprises an elongate link connecting between the table and the base and made up of first and second engaging parts movable lengthwise relative to each other and means are provided for fixing the relative lengthwise positions of the first and second link parts,
wherein the first and second links are elongate, the table fixing means includes first and second locking plates each having a through bore with an axis, one of the first and second link parts extending through the bores in the first and second locking plates, means for limiting lengthwise movement of the locking plates relative to the other of the first and second link parts and means for biasably urging the locking plates away from each other to thereby misalign the length of the one link part and the axes of the bores in the first and second link parts so that the one link part binds in the bores and is prevented from shifting relative to the locking plates.

15. The portable device according to claim 14 wherein the biasably urging means comprises a spring interposed between the locking plates to urge the locking plates away from each other.

16. The portable device according to claim 15 wherein means are provided remote from said locking plates to overcome the bias force from the spring to move the locking plates towards each other to release the table fixing means to thereby allow selective positioning of the table.

* * * * *